(12) United States Patent
Budiman

(10) Patent No.: US 8,635,046 B2
(45) Date of Patent: Jan. 21, 2014

(54) METHOD AND SYSTEM FOR EVALUATING ANALYTE SENSOR RESPONSE CHARACTERISTICS

(75) Inventor: Erwin Satrya Budiman, Fremont, CA (US)

(73) Assignee: Abbott Diabetes Care Inc., Alameda, CA (US)

(*) Notice: Subject to any disclaimer, the term of this patent is extended or adjusted under 35 U.S.C. 154(b) by 296 days.

(21) Appl. No.: 13/166,797

(22) Filed: Jun. 22, 2011

(65) Prior Publication Data

US 2011/0320167 A1    Dec. 29, 2011

Related U.S. Application Data

(60) Provisional application No. 61/357,986, filed on Jun. 23, 2010.

(51) Int. Cl.
*G06F 17/18*    (2006.01)

(52) U.S. Cl.
USPC ........... 702/179; 600/300; 600/309; 600/347; 600/365

(58) Field of Classification Search
USPC .................. 702/179; 600/300, 309, 347, 365
See application file for complete search history.

(56) References Cited

U.S. PATENT DOCUMENTS

| | | | |
|---|---|---|---|
| 3,581,062 A | 5/1971 | Aston | |
| 3,926,760 A | 12/1975 | Allen et al. | |
| 3,949,388 A | 4/1976 | Fuller | |
| 3,978,856 A | 9/1976 | Michel | |
| 4,036,749 A | 7/1977 | Anderson | |
| 4,055,175 A | 10/1977 | Clemens et al. | |
| 4,129,128 A | 12/1978 | McFarlane | |
| 4,245,634 A | 1/1981 | Albisser et al. | |
| 4,327,725 A | 5/1982 | Cortese et al. | |
| 4,344,438 A | 8/1982 | Schultz | |
| 4,349,728 A | 9/1982 | Phillips et al. | |
| 4,373,527 A | 2/1983 | Fischell | |
| 4,392,849 A | 7/1983 | Petre et al. | |
| 4,425,920 A | 1/1984 | Bourland et al. | |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

Bremer et al., Benchmark Data from the Literature for Evaluation of New Glucose Sensing Technologies, Diabetes Technology & Therapeutics, vol. 3, No. 3, 2001.*

(Continued)

*Primary Examiner* — Mohamed Charioui
*Assistant Examiner* — John Kuan
(74) *Attorney, Agent, or Firm* — Jackson & Co., LLP

(57) ABSTRACT

Apparatus, method, system and kit for receiving a plurality of continuous analyte sensor values for corresponding reference analyte values, calculating a rate of change value for the continuous analyte sensor values, defining a plurality of data range windows of the reference analyte values, evaluating the corresponding continuous analyte sensor values, the rate of change values, the reference analyte values, and/or a plurality of corresponding difference values for the plurality of data range windows, and determining a best fit based on the evaluation of the plurality of data range windows are provided.

24 Claims, 8 Drawing Sheets

(56) References Cited

U.S. PATENT DOCUMENTS

| | | |
|---|---|---|
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,634,468 A | 6/1997 | Platt et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |

(56) References Cited

U.S. PATENT DOCUMENTS

| | | |
|---|---|---|
| 6,134,461 A | 10/2000 | Say et al. |
| 6,143,164 A | 11/2000 | Heller et al. |
| 6,144,871 A | 11/2000 | Saito et al. |
| 6,159,147 A | 12/2000 | Lichter et al. |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,514,718 B2 | 2/2003 | Heller et al. |
| 6,520,326 B2 | 2/2003 | McIvor et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,016,713 B2 * | 3/2006 | Gardner et al. ............... 600/310 |
| 7,016,720 B2 | 3/2006 | Kroll |
| 7,020,508 B2 | 3/2006 | Stivoric et al. |
| 7,022,072 B2 | 4/2006 | Fox et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |

(56) References Cited

U.S. PATENT DOCUMENTS

| | | | |
|---|---|---|---|
| 7,029,444 | B2 | 4/2006 | Shin et al. |
| 7,041,068 | B2 | 5/2006 | Freeman et al. |
| 7,041,468 | B2 | 5/2006 | Drucker et al. |
| 7,043,287 | B1 | 5/2006 | Khalil et al. |
| 7,043,305 | B2 | 5/2006 | KenKnight et al. |
| 7,052,483 | B2 | 5/2006 | Wojcik |
| 7,056,302 | B2 | 6/2006 | Douglas |
| 7,058,453 | B2 | 6/2006 | Nelson et al. |
| 7,060,031 | B2 | 6/2006 | Webb et al. |
| 7,074,307 | B2 | 7/2006 | Simpson et al. |
| 7,076,300 | B1 | 7/2006 | Kroll et al. |
| 7,081,195 | B2 | 7/2006 | Simpson et al. |
| 7,082,334 | B2 | 7/2006 | Boute et al. |
| 7,092,891 | B2 | 8/2006 | Maus et al. |
| 7,096,064 | B2 | 8/2006 | Deno et al. |
| 7,098,803 | B2 | 8/2006 | Mann et al. |
| 7,103,412 | B1 | 9/2006 | Kroll |
| 7,108,778 | B2 | 9/2006 | Simpson et al. |
| 7,110,803 | B2 | 9/2006 | Shults et al. |
| 7,113,821 | B1 | 9/2006 | Sun et al. |
| 7,118,667 | B2 | 10/2006 | Lee |
| 7,123,950 | B2 | 10/2006 | Mannheimer |
| 7,125,382 | B2 | 10/2006 | Zhou et al. |
| 7,134,999 | B2 | 11/2006 | Brauker et al. |
| 7,136,689 | B2 | 11/2006 | Shults et al. |
| 7,142,911 | B2 | 11/2006 | Boileau et al. |
| 7,153,265 | B2 | 12/2006 | Vachon |
| 7,171,274 | B2 | 1/2007 | Starkweather et al. |
| 7,190,988 | B2 | 3/2007 | Say et al. |
| 7,192,450 | B2 | 3/2007 | Brauker et al. |
| 7,198,606 | B2 | 4/2007 | Boecker et al. |
| 7,203,549 | B2 | 4/2007 | Schommer et al. |
| 7,225,535 | B2 | 6/2007 | Feldman et al. |
| 7,226,978 | B2 | 6/2007 | Tapsak et al. |
| 7,228,182 | B2 | 6/2007 | Healy et al. |
| 7,237,712 | B2 | 7/2007 | DeRocco et al. |
| 7,258,673 | B2 | 8/2007 | Racchini et al. |
| 7,267,665 | B2 | 9/2007 | Steil et al. |
| 7,272,436 | B2 | 9/2007 | Gill et al. |
| 7,276,029 | B2 | 10/2007 | Goode, Jr. et al. |
| 7,278,983 | B2 | 10/2007 | Ireland et al. |
| 7,295,867 | B2 | 11/2007 | Berner et al. |
| 7,297,114 | B2 | 11/2007 | Gill et al. |
| 7,299,082 | B2 | 11/2007 | Feldman et al. |
| 7,310,544 | B2 | 12/2007 | Brister et al. |
| 7,317,938 | B2 | 1/2008 | Lorenz et al. |
| 7,318,816 | B2 | 1/2008 | Bobroff et al. |
| 7,324,850 | B2 | 1/2008 | Persen et al. |
| 7,335,294 | B2 | 2/2008 | Heller et al. |
| 7,347,819 | B2 | 3/2008 | Lebel et al. |
| 7,354,420 | B2 | 4/2008 | Steil et al. |
| 7,364,592 | B2 | 4/2008 | Carr-Brendel et al. |
| 7,366,556 | B2 | 4/2008 | Brister et al. |
| 7,379,765 | B2 | 5/2008 | Petisce et al. |
| 7,384,397 | B2 | 6/2008 | Zhang et al. |
| 7,387,010 | B2 | 6/2008 | Sunshine |
| 7,399,277 | B2 | 7/2008 | Saidara et al. |
| 7,402,153 | B2 | 7/2008 | Steil et al. |
| 7,404,796 | B2 | 7/2008 | Ginsberg |
| 7,419,573 | B2 | 9/2008 | Gundel |
| 7,424,318 | B2 | 9/2008 | Brister et al. |
| 7,460,898 | B2 | 12/2008 | Brister et al. |
| 7,467,003 | B2 | 12/2008 | Brister et al. |
| 7,471,972 | B2 | 12/2008 | Rhodes et al. |
| 7,474,992 | B2 | 1/2009 | Ariyur |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,502,644 | B2 | 3/2009 | Gill et al. |
| 7,519,408 | B2 | 4/2009 | Rasdal et al. |
| 7,524,287 | B2 | 4/2009 | Bharmi |
| 7,547,281 | B2 | 6/2009 | Hayes et al. |
| 7,565,197 | B2 | 7/2009 | Haubrich et al. |
| 7,569,030 | B2 | 8/2009 | Lebel et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,630,748 | B2 | 12/2009 | Budiman |
| 7,632,228 | B2 | 12/2009 | Brauker et al. |
| 7,637,868 | B2 | 12/2009 | Saint et al. |
| 7,640,048 | B2 | 12/2009 | Dobbles et al. |
| 7,659,823 | B1 | 2/2010 | Killian et al. |
| 7,668,596 | B2 | 2/2010 | Von Arx et al. |
| 7,699,775 | B2 | 4/2010 | Desai et al. |
| 7,699,964 | B2 | 4/2010 | Feldman et al. |
| 7,736,310 | B2 | 6/2010 | Taub et al. |
| 7,741,734 | B2 | 6/2010 | Joannopoulos et al. |
| 7,766,829 | B2 | 8/2010 | Sloan et al. |
| 7,771,352 | B2 | 8/2010 | Shults et al. |
| 7,774,145 | B2 | 8/2010 | Brauker et al. |
| 7,778,680 | B2 | 8/2010 | Goode, Jr. et al. |
| 7,779,332 | B2 | 8/2010 | Karr et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,826,981 | B2 | 11/2010 | Goode, Jr. et al. |
| 7,831,310 | B2 | 11/2010 | Lebel et al. |
| 7,860,574 | B2 | 12/2010 | Von Arx et al. |
| 7,882,611 | B2 | 2/2011 | Shah et al. |
| 7,889,069 | B2 | 2/2011 | Fifolt et al. |
| 7,899,511 | B2 | 3/2011 | Shults et al. |
| 7,905,833 | B2 | 3/2011 | Brister et al. |
| 7,912,674 | B2 | 3/2011 | Killoren Clark et al. |
| 7,914,450 | B2 | 3/2011 | Goode, Jr. et al. |
| 7,916,013 | B2 | 3/2011 | Stevenson |
| 7,955,258 | B2 | 6/2011 | Goscha et al. |
| 7,970,448 | B2 | 6/2011 | Shults et al. |
| 7,974,672 | B2 | 7/2011 | Shults et al. |
| 7,999,674 | B2 | 8/2011 | Kamen |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,111,042 | B2 | 2/2012 | Bennett |
| 8,115,488 | B2 | 2/2012 | McDowell |
| 8,116,681 | B2 | 2/2012 | Baarman |
| 8,116,683 | B2 | 2/2012 | Baarman |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Dicks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,150,321 | B2 | 4/2012 | Winter et al. |
| 8,150,516 | B2 | 4/2012 | Levine et al. |
| 8,179,266 | B2 | 5/2012 | Hermle |
| 8,216,138 | B1 | 7/2012 | McGarraugh |

(56) References Cited

U.S. PATENT DOCUMENTS

| | | |
|---|---|---|
| 8,282,549 B2 | 10/2012 | Brauker et al. |
| 2001/0041831 A1 | 11/2001 | Starkweather et al. |
| 2002/0019022 A1 | 2/2002 | Dunn et al. |
| 2002/0042090 A1 | 4/2002 | Heller et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0143266 A1 | 10/2002 | Bock |
| 2002/0143372 A1 | 10/2002 | Snell et al. |
| 2002/0161288 A1 | 10/2002 | Shin et al. |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0099529 A1 | 5/2004 | Mao et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0049179 A1 | 3/2005 | Davidson et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0214892 A1 | 9/2005 | Kovatchev et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277164 A1 | 12/2005 | Drucker et al. |
| 2005/0277912 A1 | 12/2005 | John |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |

(56) References Cited

U.S. PATENT DOCUMENTS

| | | |
|---|---|---|
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0055799 A1 | 3/2007 | Koehler et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0314395 A1 | 12/2008 | Kovatchev et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012379 A1 | 1/2009 | Goode et al. |

(56) References Cited

U.S. PATENT DOCUMENTS

| | | |
|---|---|---|
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054748 A1 | 2/2009 | Feldman |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0267765 A1 | 10/2009 | Greene et al. |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0081906 A1 | 4/2010 | Hayter et al. |
| 2010/0081909 A1 | 4/2010 | Budiman et al. |
| 2010/0141656 A1 | 6/2010 | Krieftewirth |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0190435 A1 | 7/2010 | Cook et al. |
| 2010/0191085 A1 | 7/2010 | Budiman |
| 2010/0191472 A1 | 7/2010 | Doniger et al. |
| 2010/0204557 A1 | 8/2010 | Kiaie et al. |
| 2010/0230285 A1 | 9/2010 | Hoss et al. |
| 2010/0234710 A1 | 9/2010 | Budiman et al. |
| 2010/0265073 A1 | 10/2010 | Harper et al. |
| 2010/0274515 A1 | 10/2010 | Hoss et al. |
| 2010/0277342 A1 | 11/2010 | Sicurello et al. |
| 2010/0280441 A1 | 11/2010 | Willinska et al. |
| 2010/0280782 A1 | 11/2010 | Harper et al. |
| 2010/0312176 A1 | 12/2010 | Lauer et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0077490 A1 | 3/2011 | Simpson et al. |
| 2011/0105873 A1 | 5/2011 | Feldman et al. |
| 2011/0148905 A1 | 6/2011 | Simmons et al. |
| 2011/0152637 A1 | 6/2011 | Kateraas et al. |
| 2011/0184268 A1 | 7/2011 | Taub |
| 2011/0193704 A1 | 8/2011 | Harper et al. |
| 2011/0208027 A1 | 8/2011 | Wagner et al. |
| 2011/0208155 A1 | 8/2011 | Palerm et al. |
| 2011/0224523 A1 | 9/2011 | Budiman |
| 2011/0257895 A1 | 10/2011 | Brauker et al. |
| 2011/0263958 A1 | 10/2011 | Brauker et al. |
| 2011/0320130 A1 | 12/2011 | Valdes et al. |
| 2012/0078071 A1 | 3/2012 | Bohm et al. |
| 2012/0108931 A1 | 5/2012 | Taub et al. |
| 2012/0108934 A1 | 5/2012 | Valdes et al. |
| 2012/0173200 A1 | 7/2012 | Breton et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1419731 | 5/2004 |
| EP | 0939602 | 9/2004 |
| EP | 1850909 | 4/2010 |
| EP | 1677668 | 7/2010 |
| JP | 2005-513602 | 5/2002 |
| JP | 2004-358261 | 12/2004 |

(56) References Cited

FOREIGN PATENT DOCUMENTS

| | | |
|---|---|---|
| WO | WO-96/25089 | 8/1996 |
| WO | WO-96/35370 | 11/1996 |
| WO | WO-97/15227 | 5/1997 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/74753 | 12/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/060455 | 7/2004 |
| WO | WO-2004/061420 | 7/2004 |
| WO | WO-2005/041766 | 5/2005 |
| WO | WO-2005/065542 | 7/2005 |
| WO | WO-2005/089103 | 9/2005 |
| WO | WO-2006/024671 | 3/2006 |
| WO | WO-2006/079114 | 7/2006 |
| WO | WO-2006/081336 | 8/2006 |
| WO | WO-2006/086423 | 8/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041072 | 4/2007 |
| WO | WO-2007/041248 | 4/2007 |
| WO | WO-2007/056638 | 5/2007 |
| WO | WO-2007/101223 | 9/2007 |
| WO | WO-2007/115094 | 10/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/001366 | 1/2008 |
| WO | WO-2008/021913 | 2/2008 |
| WO | WO-2008/042760 | 4/2008 |
| WO | WO-2008/052057 | 5/2008 |
| WO | WO-2008/086541 | 7/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |

OTHER PUBLICATIONS

Lodwig et al., Continuous Glucose Monitoring with Glucose Sensors: Calibration and Assessment Criteria, Diabetes Technology & Therapeutics vol. 5, No. 4, 2003.*

Panteleon et al, The Role of the Independent Variable to Glucose Sensor Calibration, Diabetes Technology & Therapeutics vol. 5, No. 3, 2003.*

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Georgescu, B., et al., "Real-Time Multimodel Tracking of Myocardium in Echocardiography Using Robust Information Fusion", *Medical Image Computing and Computer-Assisted Intervention*, 2004, pp. 777-785.

Goldman, J. M., et al., "Masimo Signal Extraction Pulse Oximetry", *Journal of Clinical Monitorin and Computing*, vol. 16, No. 7, 2000, pp. 475-483.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Maher, "A Method for Extrapolation of Missing Digital Audio Data", *Preprints of Papers Presented at the AES Convention*, 1993, pp. 1-19.

Maher, "Audio Enhancement using Nonlinear Time-Frequency Filtering", *AES 26th International Conference*, 2005, pp. 1-9.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

(56) References Cited

OTHER PUBLICATIONS

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Whipple, G., "Low Residual Noise Speech Enhancement Utilizing Time-Frequency", *Proceedings of the International Conference on Acoustics, Speech, and Signal Processing*, vol. 19, 1994, pp. 15-18.

Wilson, G. S., et al., "Progress Toward the Development of an Implantable Sensor for Glucose", *Clinical Chemistry*, vol. 38, No. 9, 1992, pp. 1613-1617.

Wolfe, P. J., et al., "Interpolation of Missing Data Values for Audio Signal Restoration Using a Gabor Regression Model", *2005 IEEE International Conference on Acoustics, Speech, and Signal Processing*, vol. 5, 2005, pp. 517-520.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", *Biosensors and Bioelectronics*, vol. 17, No. 8, 2002, pp. 647-654.

Diabetes Control and Complications Trial Research Group, "The Effect of Intensive Treatment of Diabetes on the Development and Progression of Long-Term Complications in Insulin-Dependent Diabetes Mellitus," *New England J. Med.* vol. 329, 1993, pp. 977-986.

Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582-589.

Kovatchev, B. P., et al., "Evaluating the Accuracy of Continuous Glucose-Monitoring Sensors", *Diabetes Care*, vol. 27, No. 8, 2004, pp. 1922-1928.

Kuure-Kinsey, M., et al., "A Dual-Rate Kalman Filter for Continuous Glucose Monitoring", *Proceedings of the 28th IEEE, EMBS Annual International Conference*, New York City, 2006, pp. 63-66.

Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

Panteleon, A. E., et al., "The Role of the Independent Variable to Glucose Sensor Calibration", *Diabetes Technology & Therapeutics*, vol. 5, No. 3, 2003, pp. 401-410.

Parker, R., et al., "Robust H∞ Glucose Control in Diabetes Using a Physiological Model", *AIChE Journal*, vol. 46, No. 12, 2000, pp. 2537-2549.

* cited by examiner

METHOD AND SYSTEM FOR EVALUATING ANALYTE SENSOR RESPONSE CHARACTERISTICS

RELATED APPLICATION

The present application claims the benefit of U.S. Provisional Application No. 61/357,986 filed Jun. 23, 2010 entitled "Method and System for Evaluating Analyte Sensor Response Characteristics", the disclosure of which is incorporated herein by reference for all purposes.

BACKGROUND

Benefits of a closed loop control system for treating diabetic conditions with monitoring glucose levels and adjusting delivery rate of insulin are well known. Such systems, referred to as artificial pancreas, model healthy pancreas which, when functioning normally, produces insulin (by the beta cells (β-cells)) to counteract the rise in glucose levels in the blood stream. As is known, Type-1 diabetes mellitus condition exists when the beta cells in the pancreas either die or are unable to produce sufficient amount of insulin naturally in response to the elevated glucose levels.

Common treatment of Type-1 diabetes is the use of insulin pumps that are programmed to continuously deliver insulin to the body through an infusion set. The use of insulin pumps to treat Type-2 diabetes (where the beta cells in the pancreas do produce insulin, but an inadequate quantity) is also becoming more prevalent. Such insulin delivery devices are preprogrammed with delivery rates such as basal profiles which are tailored to each user, and configured to provide the needed insulin to the user.

In addition, continuous glucose monitoring systems have been developed to provide real time monitoring of fluctuation in glucose levels. One example is the FreeStyle Navigator® Continuous Glucose Monitoring System available from Abbott Diabetes Care Inc., of Alameda, Calif. The use of such glucose monitoring systems provides the user with real time glucose level information. Using the continuous glucose monitoring system, for example, diabetics are able to determine when insulin is needed to lower glucose levels or when additional glucose is needed to raise the level of glucose.

Using a continuous glucose monitoring system in conjunction with an insulin pump can be an effective treatment tool for individuals with Type-1 or severe Type-2 diabetic condition to maintain their blood sugar levels at a physiologically desirable range. However, for the continuous glucose monitoring system to be effective, characteristics of the continuous glucose monitoring system, particularly the continuous glucose sensor of the system, must be evaluated and accurate. Evaluation of characteristics, such as linearity and lag, associated with continuous glucose sensors can impact glucose control errors and previous methods of evaluating such characteristics, such as linearity, can be confounded by lag, noise and apparent nonlinearities due to data distribution.

SUMMARY

Accordingly, a method for evaluating characteristics of a continuous analyte sensor in one aspect of the present disclosure includes receiving a plurality of continuous analyte sensor values for corresponding reference analyte values, calculating a rate of change value for the continuous analyte sensor values, defining a plurality of data range windows of the reference analyte values, evaluating the corresponding continuous analyte sensor values, the rate of change values, the reference analyte values, and/or a plurality of corresponding difference values for the plurality of data range windows, and determining a best fit based on the evaluation of the plurality of data range windows is provided.

In certain aspects, the difference value is the difference between the continuous analyte sensor value and the corresponding reference analyte value and determining the best fit includes determining a least-squares line or relationship based on a graphical representation of the rate of change of glucose values and the difference values for each of the plurality of data range windows.

Certain aspects of the present disclosure include determining a slope and an intercept of the least-squares line for each of the plurality of data range windows and determining a best fit function based on a graphical representation of the intercepts of the least-squares lines of each of the plurality of data range windows and the reference analyte values at the centers of the plurality of data range windows, where the best fit function corresponds to a linearity characteristic of the continuous analyte sensor and determining a best fit function based on a graphical representation of the slopes of the least-squares lines of each of the plurality of data range windows and the reference analyte values at the centers of the plurality of data range windows, where the best fit function corresponds to a lag characteristic of the continuous analyte sensor are provided.

Also provided are systems and kits.

INCORPORATED BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; 7,299,082; U.S. Published Application Nos. 2004/0186365; 2005/0182306; 2006/0025662; 2006/0091006; 2007/0056858; 2007/0068807; 2007/0095661; 2007/0108048; 2007/0199818; 2007/0227911; 2007/0233013; 2008/0066305; 2008/0081977; 2008/0102441; 2008/0148873; 2008/0161666; 2008/0267823; and 2009/0054748; U.S. patent application Ser. Nos. 11/461,725, now U.S. Pat. No. 7,866,026; Ser. No. 12/131,012; 12/242,823, now U.S. Pat. No. 8,219,173; Ser. No. 12/363,712, now U.S. Pat. No. 8,346,335; Ser. No. 12/495,709; 12/698,124; 12/714,439; 12/794,721; 12/848,075, now U.S. Pat. No. 8,478,557; and Ser. No. 12/842,013 and U.S. Provisional Application Ser. No. 61/347,754.

DETAILED DESCRIPTION

Figure 1:
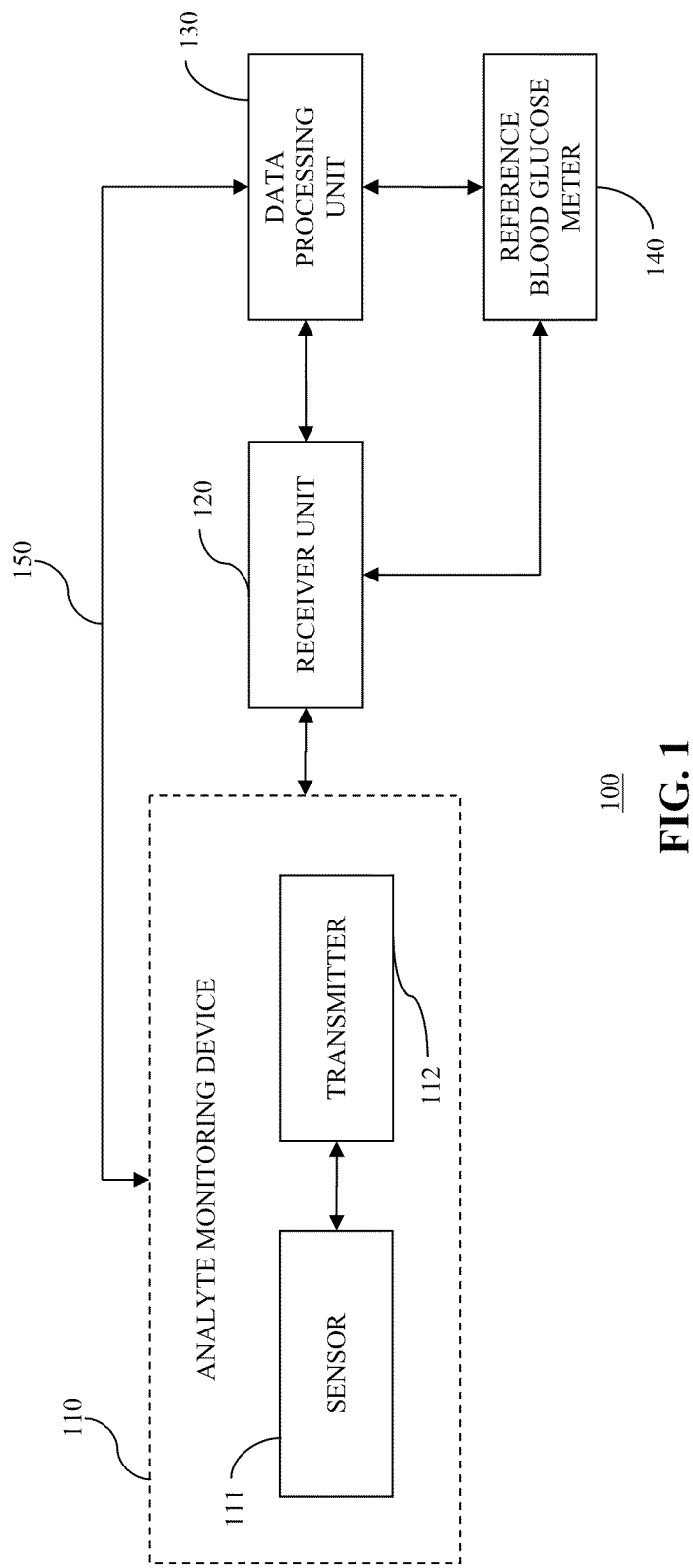
FIG. 1 is a block diagram illustrating a system for evaluating characteristics of a sensor in one or more embodiments of the present disclosure.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges as also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

As described in further detail below, in accordance with various embodiments of the present disclosure, there is provided methods and systems for evaluating the response of an analyte sensor. In particular, in certain embodiments, there are provided methods for evaluating the linearity and lag characteristics of an analyte sensor. The analyte sensor, in some embodiments, may be part of an analyte monitoring system, such as a glucose monitoring system, such as a continuous glucose monitoring system. Examples of analyte sensors and analyte monitoring systems to which the disclosed methods may be applied can be found in, for example, among others, U.S. Pat. Nos. 6,103,033, 6,134,461, 6,175,752, 6,284,478 and 6,560,471 and in U.S. patent application Ser. Nos. 12/393,921, 12/698,124 and 12/714,439, the disclosures of each of which are incorporated herein by reference in their entirety for all purposes. The analyte sensors and monitoring systems described herein are described mainly with respect to glucose sensors for use with continuous glucose monitoring systems, however, it is to be appreciated that within the scope of the present disclosure, the described methods may be applied to sensors and monitoring systems configured for detection and measurement of other analytes including, but not limited to, lactate and oxygen, and the sensors may be configured for continuous, substantially continuous, semi-continuous, or periodic measurement.

FIG. 1 is a block diagram illustrating a system for evaluating characteristics of an analyte sensor in one or more embodiments of the present disclosure. Referring to FIG. 1, in some embodiments, a system 100 for evaluating characteristics of an analyte sensor includes an analyte monitoring device 110, the analyte monitoring device 110 including an analyte sensor 111 for which characteristics are to be evaluated, and a transmitter module 112 to enable communication with one or more other devices. The system 100 may also include a receiver unit 120 in data communication with the analyte monitoring device 110 and a data processing unit 130, such as a computer or other microprocessor driven device. Other embodiments of the system 100 include a reference blood glucose meter, such as a conventional in vitro blood glucose meter 140. Example analyte monitoring systems can be found in, among others, U.S. Pat. No. 6,175,752, the disclosure of which is incorporated herein by reference for all purposes.

Referring still to FIG. 1, the analyte sensor 111 of analyte monitoring device 110, in certain embodiments, is a glucose sensor configured for the continuous monitoring of glucose level fluctuation in a patient or fluid sample. In other embodiments, the sensor may be configured to monitor other analytes, drugs, or chemicals, and may be configured for semi-continuous or periodic measurement. The sensor 111 is in communication with a transmitter module 112 of the analyte monitoring device. The transmitter module 112 is configured to transmit wirelessly or via a wired connection, data signals received from the analyte sensor 111 corresponding to the measured analyte level. In certain embodiments, the analyte monitoring device 110 includes other components (not shown) in addition to the analyte sensor 111 and transmitter module 112, including, but not limited to, one or more processing units, one or more memory units, one or more input and/or output units, a temperature detection module, and a power supply. The components of the analyte monitoring device 110 may be integrated into a single housing or, in other embodiments, may be in two or more separate housings in data communication with one another.

The analyte monitoring device 110, in certain embodiments, is in communication with a receiver unit 120 via the transmitter module 112. The receiver unit 120 is configured to process and/or display data received from the analyte monitoring device. The receiver unit 120, in some embodiments, is in communication with a data processing unit 130, which may be, among others, a personal computer or other microprocessor driven device. The data processing unit 130 may be configured to further process data received from the analyte monitoring device 110 via the receiver unit 120, or directly from the analyte monitoring device via a communication link 150. In certain embodiments, the data processing unit 130 is located at a remote location separated from the analyte monitoring device 110 and receiver unit 120 and data is transferred to the data processing unit 130 via a network, such as a local area network or a wide area network via the internet. The data processing unit 130 may further be in communication with a reference blood glucose meter 140 to receive reference values for use in data processing and evaluation. In other embodiments, reference values may be obtained from other reference devices, which may be specifically chosen based upon the desired analyte, drug, or chemical to be analyzed and evaluated.

Each element of the system 100 of FIG. 1 may be individual units, or alternatively, one or more or all of the elements may be integrated into single integrated unit. For example, the reference blood glucose meter 140 may be integrated into the receiver unit 120.

Still referring to FIG. 1, each of the data processing unit 130 and/or the receiver unit 120 or the analyte monitoring device 110 may be configured to process data received from the sensor 111. Processing data from the sensor 111 may include, among others, evaluating characteristics of the sensor 111, such as calculating lag and/or linearity of the sensor response, as will be described in further detail in conjunction with the flow chart of FIG. 2 below.

Figure 2:
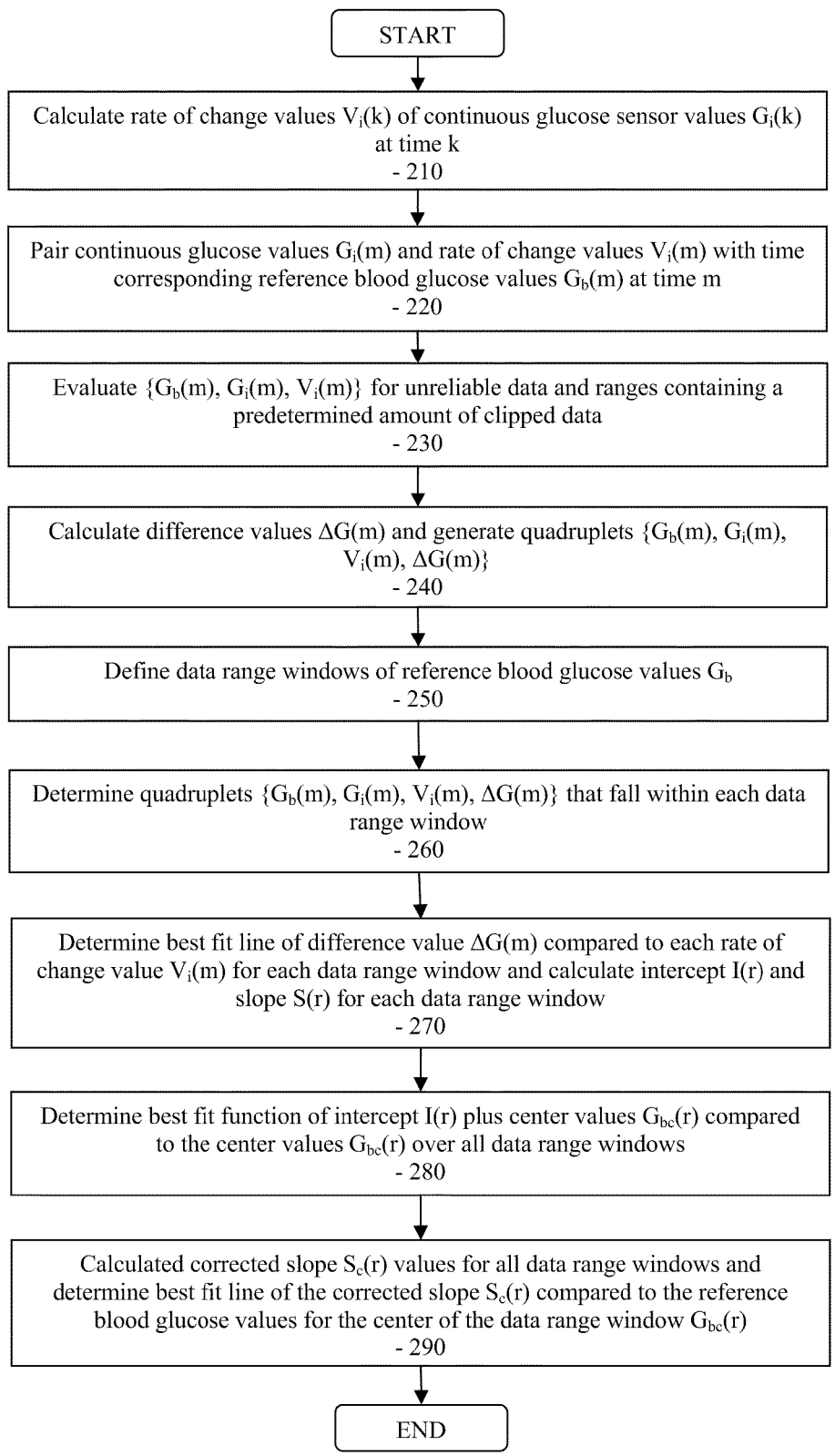
FIG. 2 is a flow chart illustrating a method for evaluating characteristics of a sensor response in one or more embodiments of the present disclosure.

FIG. 2 is a flow chart illustrating a method for evaluating characteristics of a sensor response in one or more embodiments of the present disclosure. In certain embodiments, a sensor, such as sensor 111 of FIG. 1, is a continuous glucose sensor for which the characteristics, including lag and linearity characteristics are to be evaluated. The evaluation of the sensor characteristics, in some embodiments, is carried out by the data processing unit 130 of the evaluation system 100. In other embodiments, the evaluation is carried out by the receiver unit 120. In still other embodiments, the evaluation is carried out by the analyte monitoring device 110. In accordance with still further embodiments, the evaluation is carried out by a combination of the analyte monitoring device 110, receiver unit 120, and/or the data processing unit 130.

Referring back to FIG. 2, the rate of change of a measured analyte (e.g., glucose) level as measured by the continuous glucose sensor, such as analyte sensor 111 of system 100 of FIG. 1, at a given time k, is determined (210). The rate of change at time k, $V_i(k)$, can be calculated, in one embodiment, by choosing or selecting a measurement window with half window $N_{hr}$, such that the analyte level values as measured by the continuous glucose sensor $G_i(k)$, in the window are collected $\{G_i(k-N_{hr}), \ldots G_i(k-1), G_i(k), G_i(k+1), \ldots G_i(k+N_{hr})\}$, and an average rate of change of the analyte level is computed or determined from these points.

In certain embodiments the half window $N_{hr}$ is between 1 and 15 minutes with a measurement window of between 3 and 31 minutes, however, it is to be appreciated that the window could be less than 3 minutes or greater than 31 minutes. In some embodiments, the measurement window duration needed for an accurate rate calculation may be based on the sensor type, such that, for example, a continuous, substantially continuous, or semi-continuous sensor which outputs measured analyte levels at a faster rate than an intermittent or periodic sensor, may require a shorter measurement window duration to obtain enough data points for an accurate rate of change calculation, while a periodic sensor may require a longer measurement window duration in order to obtain enough data points for an accurate rate of change calculation. In another embodiment, the rate of change at time k, $V_i(k)$, can be calculated from the slope of a best fit line, such as a least-squares error line, of the points $\{G_i(k-N_{hr}), \ldots G_i(k-1), G_i(k), G_i(k+1), \ldots G_i(k+N_{hr})\}$. In certain embodiments, the rate of change at time k, $V_i(k)$, is calculated by taking two neighboring points $G_i(k-N_{hr})$ and $G_i(k+N_{hr})$, that are half-window $N_{hr}$ samples before and after the glucose level value $G_i(k)$, respectively, and then computing the slope between these two neighboring points.

Figure 3:
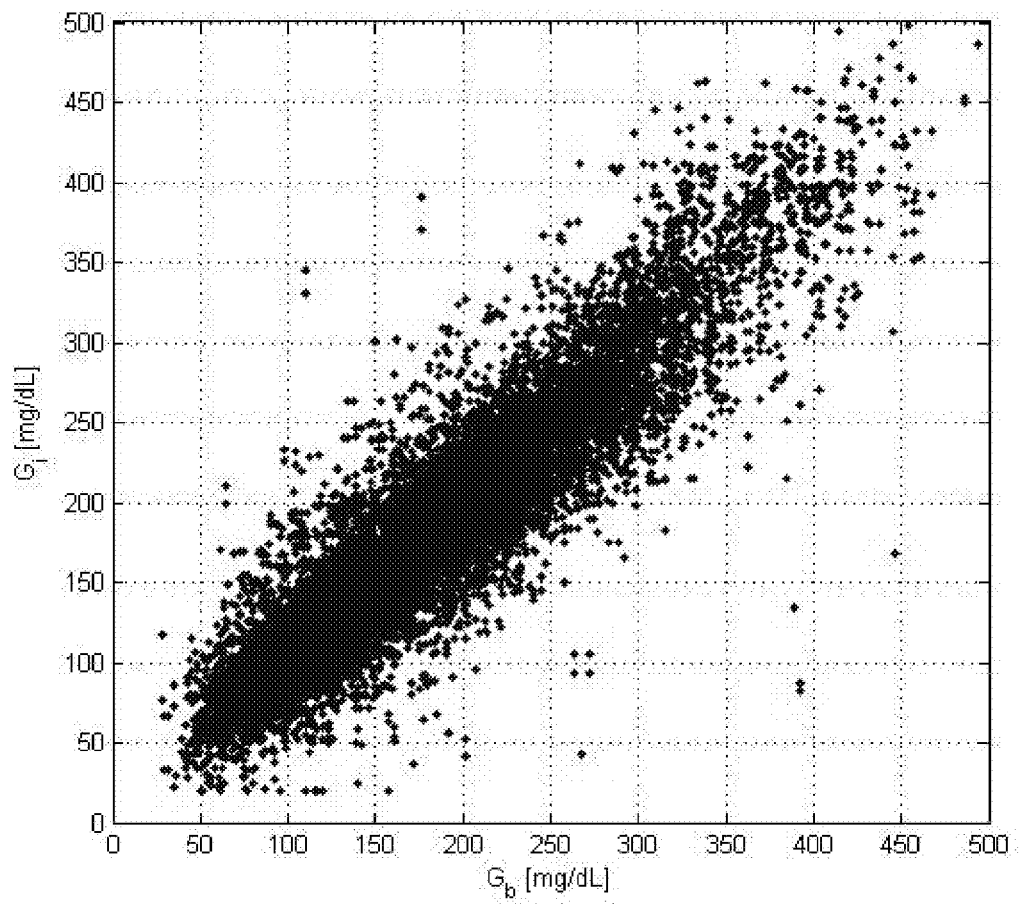
FIG. 3 is a plot illustrating a sample data set of continuous glucose values and corresponding reference blood glucose values taken at time instances m.

Referring still to FIG. 2, after determination of the rate of change calculation of the continuous glucose sensor (210), the rate of change values $V_i(m)$, and the continuous glucose sensor values $G_i(m)$ at time m are matched with reference blood glucose values $G_b(m)$, at time m (220). Matching the rate of change value and continuous glucose sensor value and the reference blood glucose value at time m generates triplets $\{G_b(m), G_i(m), V_i(m)\}$. Reference blood glucose values can be obtained in a variety of ways including measuring a blood glucose value in vitro by applying a blood sample to a test strip and measuring the blood glucose value with a conventional blood glucose monitor, such as the reference blood glucose meter 140 of FIG. 1. FIG. 3 is a plot illustrating a sample data set of continuous glucose values and corresponding reference blood glucose values taken at time instances m. For each of these pairs of matched continuous glucose sensor values $G_i(m)$, and reference blood glucose values $G_b(m)$, a corresponding continuous glucose rate of change value $V_i(m)$, also exists.

Turning back to FIG. 2, in certain embodiments, once the data set of triplets of $\{G_b(m), G_i(m), V_i(m)\}$ is determined, the triplets are evaluated to determine which triplets are considered reliable data and which triplets are to be excluded due to unreliability (230). In certain embodiments, the evaluation of the triplets may be based on stratified evaluations of the triplet data taken over predetermined ranges of reference blood glucose values $G_b$, i.e., wherein each of the predetermined ranges of reference blood glucose values are evaluated individually for the evaluation of the triplets. As such, the evaluations are performed individually on a plurality of groups of reference blood glucose values in order to determine the final result. Furthermore, in certain embodiments, evaluation of each individual range may be utilized for various weighted analysis as described in further detail below. From within each range of reference blood glucose values, the continuous glucose values are evaluated to determine if upper limit or lower limit clipping has occurred. In some embodiments, in evaluated ranges of reference blood glucose values where a significant number of triplets include continuous glucose sensor values $G_i$ that are clipped at the upper or lower range, these ranges of reference blood glucose values $G_b$ are excluded from the data set. Upper and lower clipping limits may be determined based upon the particular sensor being evaluated. For example, the lower clipping limit, in one sensor embodiment, may be 20 mg/dL and the upper clipping limit may be 500 mg/dL. Further, in certain embodiments, if the number of available continuous glucose value data points within a certain reference blood glucose value $G_b$ range is less than a predetermined amount, for example, 100 data points, then these ranges are also excluded from the data set. In another embodiment, the excluded ranges of reference blood glucose values where a significant number of continuous glucose sensor values $G_i$ are clipped, can be replaced by the statistical method of left and right censoring.

Figure 4:
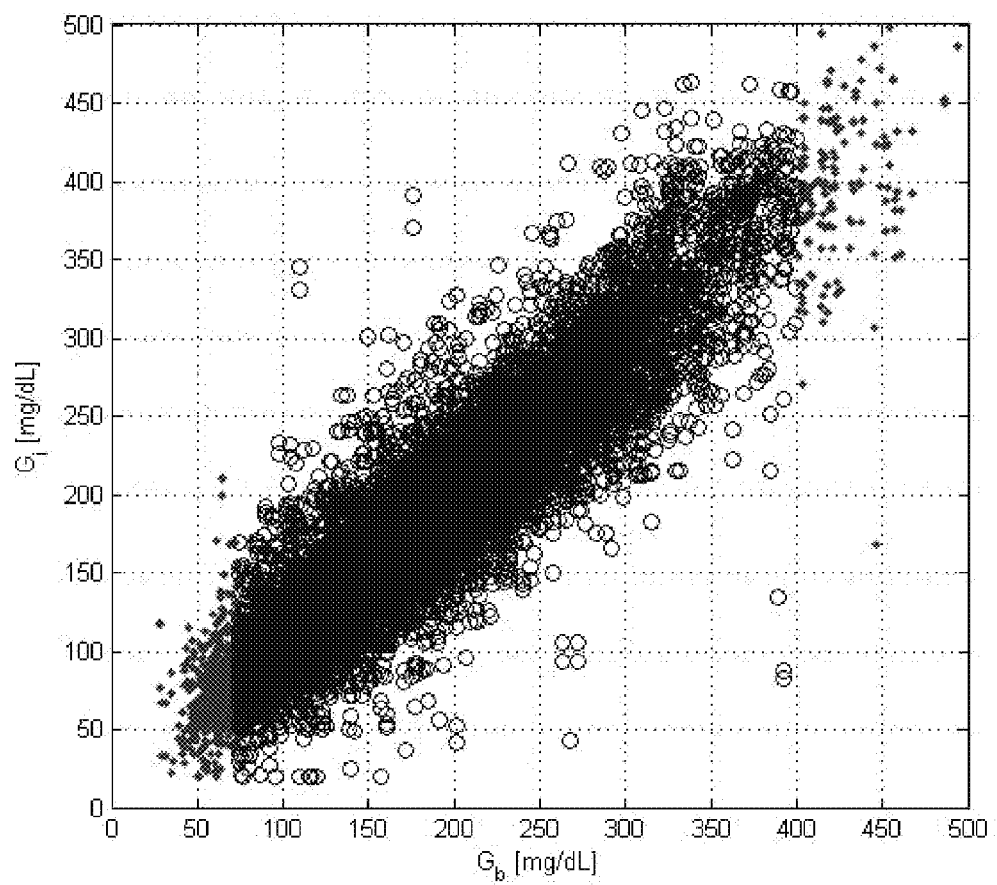
FIG. 4 is a plot illustrating the sample data set of FIG. 3 with indication of excluded ranges of reference blood glucose values.

As illustrated in FIG. 4, the sample data set of FIG. 3 was evaluated for ranges of reference blood glucose values where substantial clipping occurred and ranges of reference blood glucose values where insufficient continuous glucose data points were present. The result of the evaluation of the sample data set was reference blood glucose values $G_b$, that fell between 70 mg/dL and 400 mg/dL were evaluated as reliable and the ranges of reference blood glucose values below 70 mg/dL and above 400 mg/dL were excluded from the data set.

Returning to FIG. 2, once the data set of triplets of {$G_b(m)$, $G_i(m)$, $V_i(m)$} is evaluated and ranges of reference blood glucose values $G_b$ are excluded, for example, but not limited to, due to evaluated unreliability as described above, the difference between each continuous glucose sensor value $G_i(m)$ and reference blood glucose value $G_b(m)$ is calculated for all the non-excluded triplets, whereby the difference value $\Delta G(m)$ is determined as follows: $\Delta G(m) = G_i(m) - G_b(m)$. These difference values $\Delta G(m)$ are matched with the corresponding triplets, and quadruplets {$G_b(m)$, $G_i(m)$, $V_i(m)$, $\Delta G(m)$} are generated (240).

Still referring to FIG. 2, data range windows of the reference blood glucose values $G_b$, are defined (250) based on the reference glucose values $G_b$ that were not excluded due to unreliability because of clipping and/or lack of available data points. In certain embodiments, these data range windows of reference blood glucose values $G_b$ are used for stratified analysis of the continuous glucose data when compared with the corresponding reference blood glucose data. The stratified analysis allows for individual analysis and evaluation of the continuous glucose data for each of the corresponding data range windows of reference blood glucose values. As such, the evaluations are performed individually on a plurality of groups of reference blood glucose values in order to determine the final result. Furthermore, in certain embodiments, evaluation of each individual data range window may be utilized for various weighted analysis as described in further detail below. The data range windows may be defined based on the overall data range of values, the number of continuous glucose data values available, or other factors. In one embodiment, the data range windows may be defined as 30 mg/dL data range windows beginning at the lowest non-excluded limit of the reference glucose values $G_b$.

Figure 5:
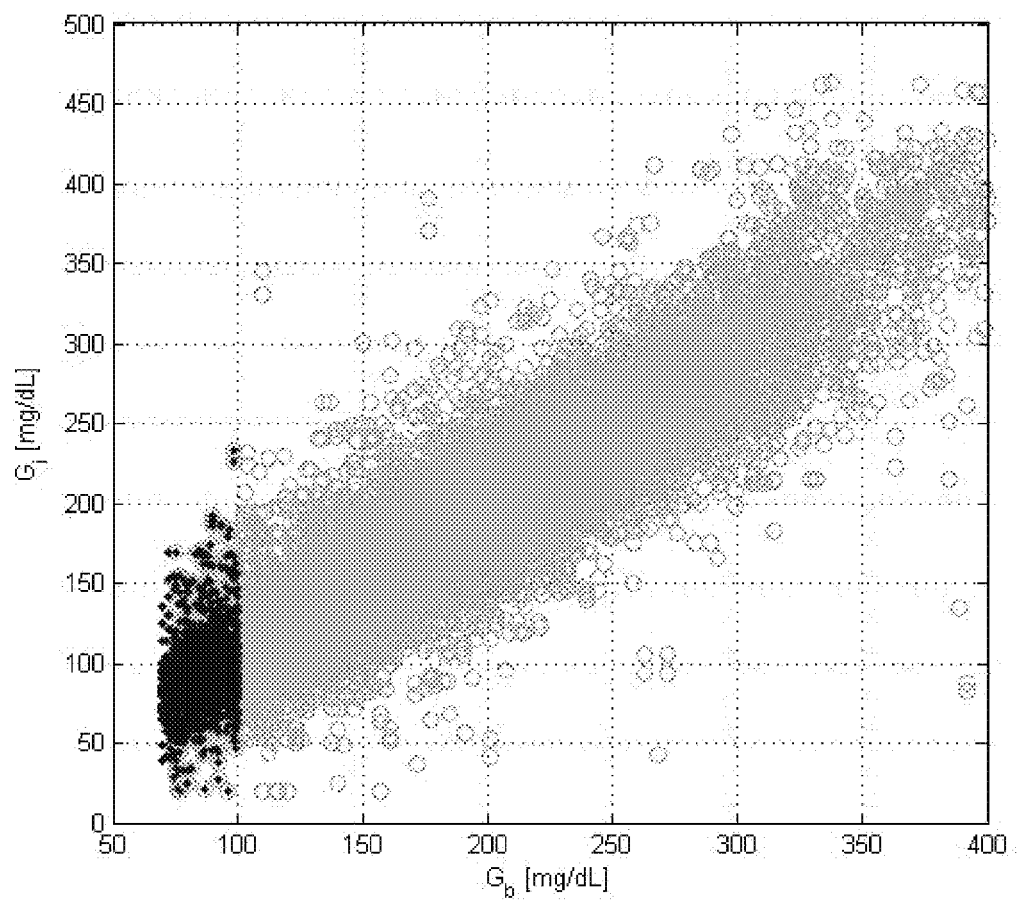
FIG. 5 is a plot illustrating a range window of 70 mg/dL to 100 mg/dL of reference glucose values $G_b(m)$ for the sample data set of FIG. 3.

Referring to FIG. 5, if a data range window of 30 mg/dL is defined, the first data range window of the sample data set of FIGS. 3 and 4 may be from 70 mg/dL to 100 mg/dL. Further, the next data range window may be from 100 mg/dL to 130 mg/dL and so on until the ranges reach the upper non-excluded limit of reference glucose value $G_b$. In certain embodiments, the data range windows may overlap, such that a first data range window is from 70 mg/dL to 100 mg/dL and the next data range window is from 80 mg/dL to 110 mg/dL and so on until the upper non-excluded limit of the reference glucose values $G_b$ is reached. Within each data range window of the reference glucose values $G_b$, there is a center reference blood glucose value, $G_{bc}(r)$. For example, the data range window from 70 mg/dL to 100 mg/dL would have a center reference blood glucose value $G_{bc}(r)$ of 85 mg/dL.

For the data set of FIGS. 3 and 4, in one embodiment, the data range window may be defined as 30 mg/dL, and data range center reference blood glucose value $G_{bc}(r)$ values are at 85, 95, . . . , 375 mg/dL. This also defines the left edges (lower range limit), $G_{bl}(r)$ to 70, 80, . . . , 360 mg/dL and the right edges (upper range limit), $G_{br}(r)$ to 100, 110, . . . , 390 mg/dL. The decision for the distance between the centers of the data range windows, and the amount of overlap (from 0 to almost 100%) may depend on the tradeoff between desired data range resolution (e.g. coarse data range resolution resulting in larger distance between the centers), the allowed maximum correlation between consecutive data ranges (e.g. a smaller allowed maximum correlation results in a smaller allowed percentage of overlap), the available number of data points of the data set used to perform the analysis (e.g. a larger data set allows for shorter distance between the centers of the data range windows and/or smaller amount of overlap), and the type of distribution to be fitted on the data. Appropriate tradeoffs in order to determine the proper distance between the centers of the data range windows and the amount of overlap amongst them would be apparent to those skilled in the art based upon the data set to be evaluated.

Referring back to FIG. 2, once the data range windows for the stratified analysis are defined, for each data range value r, where data range value r is the value of the data range window where data is being evaluated or analyzed, the quadruplets of {$G_b(m)$, $G_i(m)$, $V_i(m)$, $\Delta G(m)$} that fall within each data range window are determined (260). Thus, the quadruplets, with reference blood glucose value at time m $G_b(m)$ values that are no smaller than the lower range limit $G_{bl}$ and no greater than the upper range limit $G_{br}$, are collected for the particular data range window. Referring again to FIG. 5, as shown, the quadruplets with reference blood glucose value at time m $G_b(m)$ values between 70 mg/dL and 100 mg/dL are collected in the data range window with reference blood glucose value for the center of the data range $G_{bc}(r)=85$ mg/dL.

Figure 6:
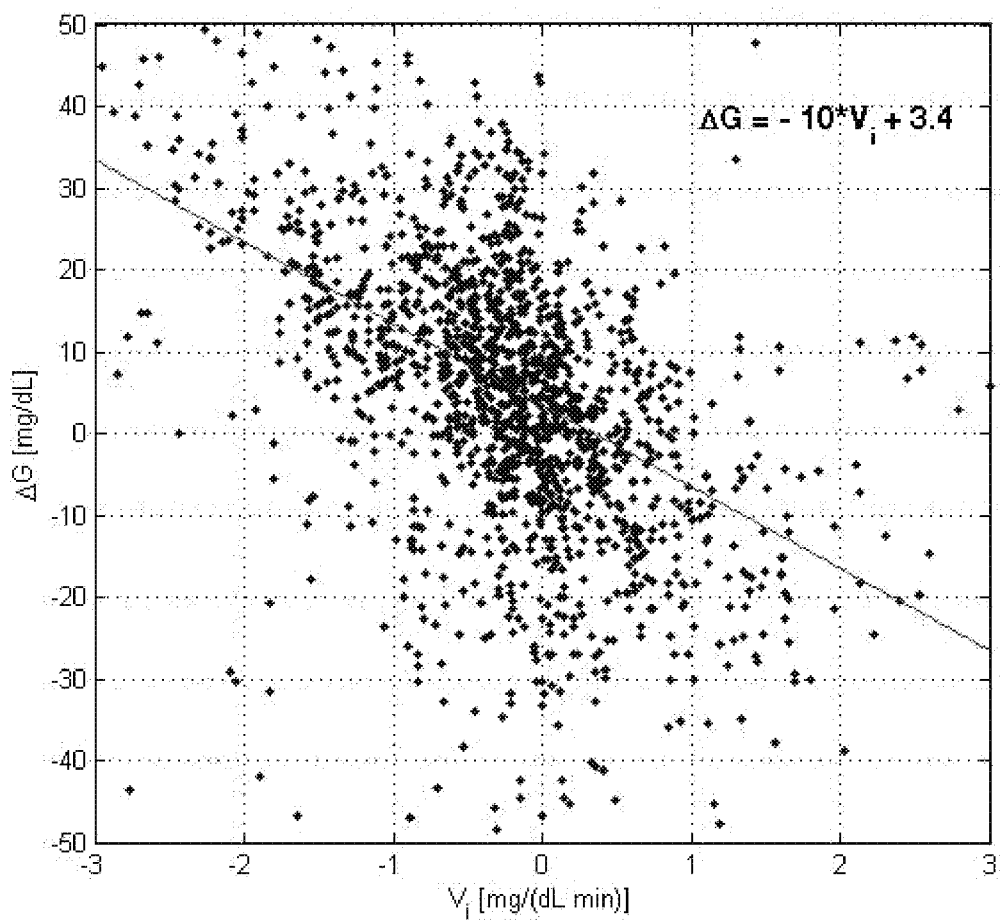
FIG. 6 illustrates a best fit line for the range of 70 mg/dL to 100 mg/dL of reference glucose values $G_b(m)$ for the sample data set of FIG. 3.

Once the quadruplets of a particular data range window are determined, a best fit line of the difference value $\Delta G(m)$ compared to each rate of change value $V_i(m)$ for the data range window is determined (270). In certain embodiments, the best fit line is calculated by setting the rate of change values $V_i(m)$ to be on the x-axis and the corresponding difference value, $\Delta G(m)$, to be on the y-axis of a scatter plot for a particular data range window and performing a least-squares error fit of a line between the points. The least-squares analysis minimizes the sum of the squared residuals of the points and calculates the best fit line of the points. From the least-squares best fit line, the intercept I(r) and slope S(r) of the particular data range window can be calculated. Further, the number of quadruplets that fall within the data range window N(r), can be determined. It will be appreciated by one skilled in the art that the best fit line may be determined using a variety of functions in addition to or in lieu of a least-squares analysis, and the best fit line may be a linear function, an exponential function, a constant, or any other function type. FIG. 6 illustrates a best fit line for the data range window of 70 mg/dL to 100 mg/dL of reference blood glucose value $G_b(m)$ for the sample data set of FIG. 3. As can be seen in the Figure, for the data range center reference blood glucose value $G_{bc}(r)=85$ mg/dL (i.e. quadruplets where the reference blood glucose $G_b(m)$ value is between 70 mg/dL and 100 mg/dL), the intercept I(r) and the slope S(r) are, I(r)=3.4 and S(r)=−10, respectively.

Referring still to FIG. 2, once the best fit lines of each data range window with center reference blood glucose value $G_{bc}(r)$ are calculated and each corresponding intercept I(r) and slope S(r) are determined, the intercept I(r) values are plotted against the corresponding reference blood glucose values for the centers of the data range windows $G_{bc}(r)$ over all the data range windows. A best fit function or line of a scatter plot of all the intercept values plus the data range center reference blood glucose values I(r)+$G_{bc}(r)$ compared to the data range center reference blood glucose values $G_{bc}(r)$ over all the data range windows is determined (280). For the sample data set of FIG. 3, the best fit function may be an affine function or a linear function with an offset, which would suggest a good coherence with a straight line, i.e. a substantially linear response.

Figure 7:
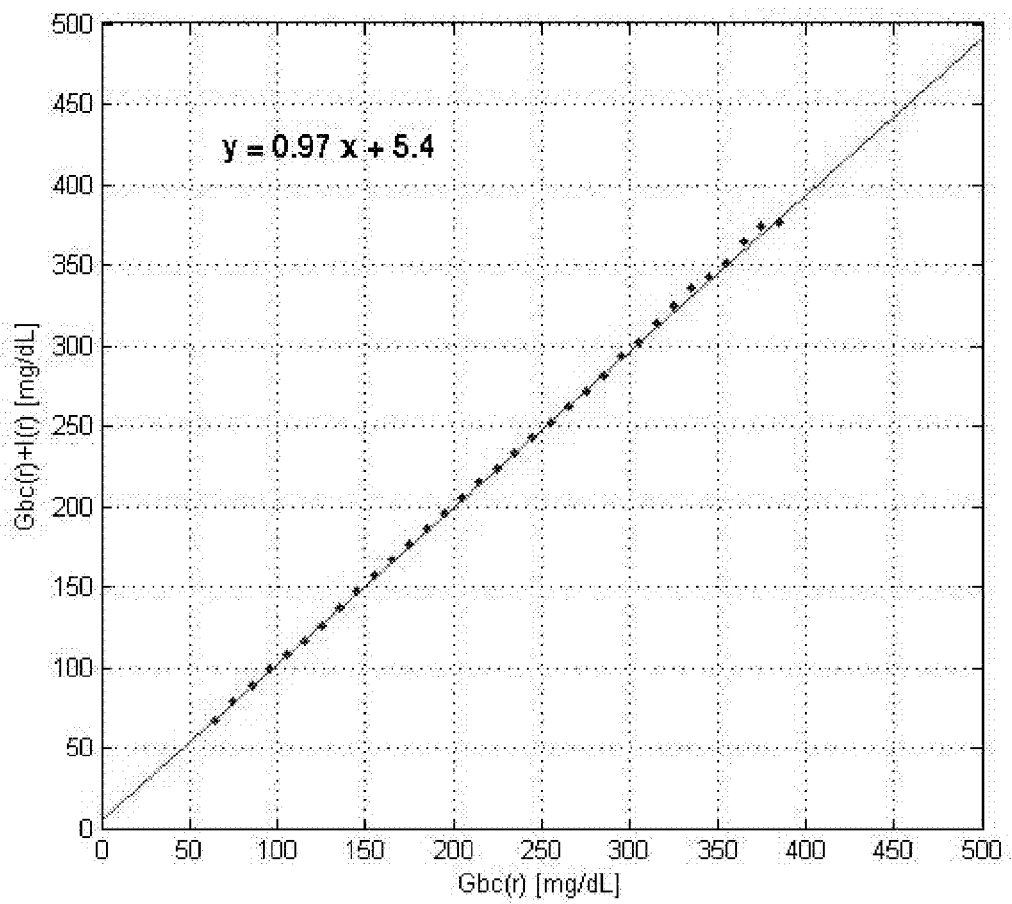
FIG. 7 illustrates a weighted best fit line for the intercepts of the ranges $G_{bc}(r)$ for the sample data set of FIG. 3.

As shown in FIG. 7, when data range window center reference blood glucose values $G_{bc}(r)$ are taken on the x-axis and corresponding intercept values plus the data range center reference blood glucose values $I(r)+G_{bc}(r)$ are taken on the y-axis of a graphical representation or plot, if a weighted least-squares best fit straight line is taken between all the points, where the weighting of the least-squares analysis is taken by the number of quadruplets associated with each data range window $N(r)$, the fitness of the line and corresponding affine function of y=0.97x+5.4, validates the linearity of the sensor response of the sensor associated with the data of the sample data set of FIG. 3. For this sample data set, an $R^2$ value of 0.9998 is obtained when an affine function is assumed to be the static response of the sensor. In certain embodiments, the determination of the coefficient of determination, $R^2$, for a least squares fit of a straight line, is identical to the calculation of the correlation coefficient between the horizontal and vertical axis values of the data points. The calculation of $R^2$ is standard practice in statistical methods. In other embodiments, the weights of the weighted least-squares analysis may include scaling by the number of points in each range, scaling by the inverse of the square of the standard error of the intercept in each range, and scaling by the inverse of the square of the standard deviation of the intercept in each range.

In certain embodiments, if the best fit function to data points of intercept values plus the data range center reference blood glucose values $I(r)+G_{bc}(r)$ compared to data range center reference blood glucose values $G_{bc}(r)$ is determined to be not substantially linear, or not an affine function or straight line with an offset, this may be an indication that the response of the sensor being evaluated is not a linear response.

Figure 8:
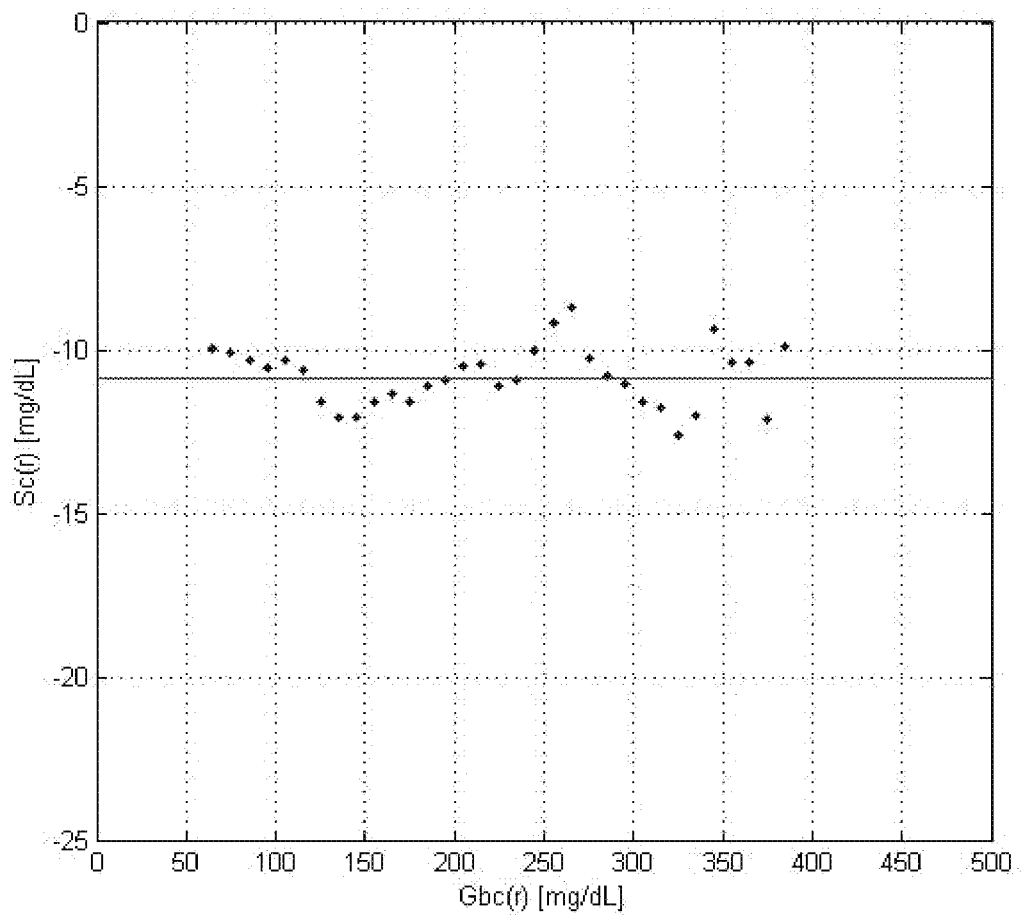
FIG. 8 illustrates a corrected slope value over the ranges $G_{bc}(r)$ for the sample data set of FIG. 3.

Returning to FIG. 2, a static response corrected slope $S_c(r)$ is calculated for each data range window based on the slope $S(r)$ and intercept $I(r)$ for each data range window center reference blood glucose value $G_{bc}(r)$ (290). In some embodiments, the corrected slope $S_c(r)$ is calculated as: $S_c(r)=S(r)*G_{bc}(r)/I(r)$. As illustrated in FIG. 8, a scatter plot of corrected slope $S_c(r)$ values over reference blood glucose at the center of data range window $G_{bc}(r)$ values suggests a constant value across the data range windows of the sample data set of FIG. 3. A weighted average, with the number of quadruplets of each data range $N(r)$ as the weight, may be used to estimate an overall time constant of the lag of the sensor. In some embodiments, the standard error of the weighted average reflects the consistency of the sensor lag over the reference glucose value $G_b$ range. In certain embodiments, the weights of the weighted average include scaling by the number of points in each range, scaling by the inverse of the square of the standard error of the intercept in each range, and scaling by the inverse of the square of the standard deviation of the intercept in each range.

In the manner described above, in certain embodiments, analyte sensor characteristics, including sensor lag and sensor linearity, can be determined for a sensor by utilizing sensor data and the methods described above. Determination of these sensor characteristics may be used, in some embodiments, for, for example, artificial pancreas use, such as the user of an insulin pump or insulin dosing for a patient with Type-1 diabetes utilizing an insulin pump in communication with a continuous glucose monitoring system and associated continuous glucose sensor.

In one aspect of the present disclosure, method for evaluating characteristics of a continuous analyte sensor includes receiving a plurality of continuous analyte sensor values for corresponding reference analyte values, calculating a rate of change value for the continuous analyte sensor values, defining a plurality of data range windows of the reference analyte values, evaluating the corresponding continuous analyte sensor values, the rate of change values, the reference analyte values, and/or a plurality of corresponding difference values for the plurality of data range windows, and determining a best fit based on the evaluation of the plurality of data range windows.

In one embodiment, the difference value is the difference between the continuous analyte sensor value and the corresponding reference analyte value.

In another embodiment, determining the best fit includes determining a least-squares line based on a graphical representation of the rate of change values and the difference values for each of the plurality of data range windows.

A further embodiment includes determining a slope and an intercept of the least-squares line for each of the plurality of data range windows.

Another further embodiment includes determining a best fit function based on a graphical representation of the intercepts of the least-squares lines of each of the plurality of data range windows and the reference analyte values at the centers of the plurality of data range windows, wherein the best fit function corresponds to a linearity characteristic of the continuous analyte sensor.

In one embodiment, determining the best fit function includes determining a best fit function based on a weighted graphical representation of the intercepts of the least-squares lines of each of the plurality of data range windows and the reference analyte values at the centers of the plurality of data range windows.

In another embodiment, the weighted graphical representation includes scaling by the number of points in each data range window, scaling by the inverse of the square of the standard error of the slope in each data range window, or scaling by the inverse of the square of the standard deviation of the slope in each data range window.

A further embodiment includes determining a best fit function based on a graphical representation of the slopes of the least-squares lines of each of the plurality of data range windows and the reference analyte values at the centers of the plurality of data range windows, wherein the best fit function corresponds to a lag characteristic of the continuous analyte sensor.

In one embodiment, determining the best fit function includes determining a best fit function based on a weighted graphical representation of the slopes of the least-squares lines of each of the plurality of data range windows and the reference analyte values at the centers of the plurality of data range windows.

In another embodiment, the weighted graphical representation includes scaling by the number of points in each data range window, scaling by the inverse of the square of the standard error of the slope in each data range window, or scaling by the inverse of the square of the standard deviation of the slope in each data range window.

Another further embodiment includes determining a corrected slope for each of the slopes of the least-squares lines of each of the plurality of data range windows and determining a best fit function based on a graphical representation of the corrected slopes of the least-squares lines of each of the plurality of data range windows and the reference analyte values at the centers of the plurality of data range windows, wherein the best fit function corresponds to a lag characteristic of the continuous analyte sensor.

In one embodiment, the corrected slope is determined based on weighted slopes of the least-squares lines of each of the plurality of data range windows.

In another aspect of the present disclosure, an apparatus for evaluating characteristics of a continuous analyte sensor includes one or more processors; and a memory operatively coupled to the one or more processors, the memory storing instructions which, when executed by the one or more processors, causes the one or more processors to receive a plurality of continuous analyte sensor values for corresponding reference analyte values, calculate a rate of change value for the continuous analyte sensor values, define a plurality of data range windows of the reference analyte values, evaluate the corresponding continuous analyte sensor values, the rate of change values, the reference analyte values, and/or a plurality of corresponding difference values for the plurality of data range windows, and determine a best fit based on the evaluation of the plurality of data range windows.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method, comprising:
receiving a plurality of analyte sensor values for a corresponding plurality of reference analyte values from an analyte sensor;
calculating a rate of change value for each of the plurality of analyte sensor values;
defining a plurality of data range windows corresponding to the plurality of reference analyte values;
evaluating, using one or more processors, the plurality of data range windows by evaluating one or more of the plurality of analyte sensor values, the rate of change values, the plurality of reference analyte values, or a plurality of corresponding difference values;
determining, using the one or more processors, a best fit based on the evaluation of the plurality of data range windows, wherein determining the best fit includes determining a least-squares line based on a graphical representation of the rate of change values and the difference values for each of the plurality of data range windows;
determining, using the one or more processors, a slope and an intercept of the least-squares line for each of the plurality of data range windows; and
determining, using the one or more processors, a best fit function based on a graphical representation of the intercepts of the least-squares lines of each of the plurality of data range windows and the reference analyte values at centers of the plurality of data range windows, wherein the best fit function corresponds to a linearity characteristic of the analyte sensor.

2. The method of claim 1, wherein the difference value is a difference between an analyte sensor value and a corresponding reference analyte value.

3. The method of claim 1, wherein determining the best fit function includes determining a best fit function based on a weighted graphical representation of the intercepts of the least-squares lines of each of the plurality of data range windows and the reference analyte values at the centers of the plurality of data range windows.

4. The method of claim 3, wherein the weighted graphical representation includes scaling by a number of points in each data range window, scaling by an inverse of a square of a standard error of the slope in each data range window, or scaling by the inverse of the square of the standard deviation of the slope in each data range window.

5. The method of claim 1, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

6. A method, comprising:
receiving a plurality of analyte sensor values for a corresponding plurality of reference analyte values from an analyte sensor;
calculating a rate of change value for each of the plurality of analyte sensor values;
defining a plurality of data range windows corresponding to the plurality of reference analyte values;
evaluating, using one or more processors, the plurality of data range windows by evaluating one or more of the plurality of analyte sensor values, the rate of change values, the plurality of reference analyte values, or a plurality of corresponding difference values;
determining, using the one or more processors, a best fit based on the evaluation of the plurality of data range windows, wherein determining the best fit includes determining a least-squares line based on a graphical representation of the rate of change values and the difference values for each of the plurality of data range windows;
determining, using the one or more processors, a slope and an intercept of the least-squares line for each of the plurality of data range windows; and
determining, using the one or more processors, a best fit function based on a graphical representation of the slopes of the least-squares lines of each of the plurality of data range windows and the reference analyte values at centers of the plurality of data range windows, wherein the best fit function corresponds to a lag characteristic of the analyte sensor.

7. The method of claim 6, wherein determining the best fit function includes determining a best fit function based on a weighted graphical representation of the slopes of the least-squares lines of each of the plurality of data range windows and the reference analyte values at the centers of the plurality of data range windows.

8. The method of claim 7, wherein the weighted graphical representation includes scaling by a number of points in each data range window, scaling by an inverse of a square of a standard error of the slope in each data range window, or scaling by the inverse of the square of a standard deviation of the slope in each data range window.

9. The method of claim 7, wherein a corrected slope is determined based on weighted slopes of the least-squares lines of each of the plurality of data range windows.

10. The method of claim 6, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

11. A method, comprising:
receiving a plurality of analyte sensor values for a corresponding plurality of reference analyte values from an analyte sensor;
calculating a rate of change value for each of the plurality of analyte sensor values;
defining a plurality of data range windows corresponding to the plurality of reference analyte values;
evaluating, using one or more processors, the plurality of data range windows by evaluating one or more of the plurality of analyte sensor values, the rate of change values, the plurality of reference analyte values, or a plurality of corresponding difference values;
determining, using the one or more processors, a best fit based on an evaluation of the plurality of data range windows, wherein determining the best fit includes determining a least-squares line based on a graphical representation of the rate of change values and the difference values for each of the plurality of data range windows;
determining, using the one or more processors, a slope and an intercept of the least-squares line for each of the plurality of data range windows; and
determining, using the one or more processors, a corrected slope for each of the slopes of the least-squares lines of each of the plurality of data range windows and determining a best fit function based on a graphical representation of the corrected slopes of the least-squares lines of each of the plurality of data range windows and the reference analyte values at centers of the plurality of data range windows, wherein the best fit function corresponds to a lag characteristic of the continuous analyte sensor.

12. The method of claim 11, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

13. An apparatus, comprising:
one or more processors; and
a memory operatively coupled to the one or more processors, the memory storing instructions which, when executed by the one or more processors, causes the one or more processors to receive a plurality of analyte sensor values for a corresponding plurality of reference analyte values from an analyte sensor, calculate a rate of change value for each of the plurality of analyte sensor values, define a plurality of data range windows corresponding to the plurality of reference analyte values, evaluate the plurality of data range windows by evaluating one or more of the plurality of analyte sensor values, the rate of change values, the plurality of reference analyte values, or a plurality of corresponding difference values for the plurality of data range windows, determine a best fit based on an evaluation of the plurality of data range windows, wherein the instructions to determine the best fit includes instructions to determine a least-squares line based on a graphical representation of the rate of change values and the difference values for each of the plurality of data range windows, determine a slope and an intercept of the least-squares line for each of the plurality of data range windows, and determine a best fit function based on a graphical representation of the intercepts of the least-squares lines of each of the plurality of data range windows and the reference analyte values at centers of the plurality of data range windows, wherein the best fit function corresponds to a linearity characteristic of the analyte sensor.

14. The apparatus of claim 13, wherein the difference value is the difference between an analyte sensor value and a corresponding reference analyte value.

15. The apparatus of claim 13, wherein the instructions to determine the best fit function includes instructions to determine a best fit function based on a weighted graphical representation of the intercepts of the least-squares lines of each of the plurality of data range windows and the reference analyte values at the centers of the plurality of data range windows.

16. The apparatus of claim 15, wherein the weighted graphical representation includes scaling by a number of points in each data range window, scaling by an inverse of a square of a standard error of the slope in each data range window, or scaling by the inverse of a square of the standard deviation of the slope in each data range window.

17. The apparatus of claim 13, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

18. An apparatus, comprising:
one or more processors; and
a memory operatively coupled to the one or more processors, the memory storing instructions which, when executed by the one or more processors, causes the one or more processors to receive a plurality of analyte sensor values for a corresponding plurality of reference analyte values from an analyte sensor, calculate a rate of change value for each of the plurality of analyte sensor values, define a plurality of data range windows corresponding to the plurality of reference analyte values, evaluate the plurality of data range windows by evaluating one or more of the plurality of analyte sensor values, the rate of change values, the plurality of reference analyte values, or a plurality of corresponding difference values, determine a best fit based on the evaluation of the plurality of data range windows, wherein the instructions to determine the best fit includes instructions to determine a least-squares line based on a graphical representation of the rate of change values and the difference values for each of the plurality of data range windows, determine a slope and an intercept of the least-squares line for each of the plurality of data range windows, and determine a best fit function based on a graphical representation of the slopes of the least-squares lines of each of the plurality of data range windows and the reference analyte values at centers of the plurality of data range windows, wherein the best fit function corresponds to a lag characteristic of the analyte sensor.

19. The apparatus of claim 18, wherein the instructions to determine the best fit function includes instructions to determine a best fit function based on a weighted graphical representation of the slopes of the least-squares lines of each of the plurality of data range windows and the reference analyte values at the centers of the plurality of data range windows.

20. The apparatus of claim 19, wherein the weighted graphical representation includes scaling by a number of points in each data range window, scaling by an inverse of a square of a standard error of the slope in each data range window, or scaling by the inverse of the square of a standard deviation of the slope in each data range window.

21. The apparatus of claim 18, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

22. An apparatus, comprising:
one or more processors; and
a memory operatively coupled to the one or more processors, the memory storing instructions which, when executed by the one or more processors, causes the one or more processors to receive a plurality of analyte sensor values for a corresponding plurality of reference analyte values from an analyte sensor, calculate a rate of change value for each of the plurality of analyte sensor values, define a plurality of data range windows corresponding to the plurality of reference analyte values, evaluate the plurality of data range windows by evaluating one or more of the plurality of analyte sensor values, the rate of change values, the plurality of reference analyte values, or a plurality of corresponding difference values, determine a best fit based on the evaluation of the plurality of data range windows, wherein the instructions to determine the best fit includes instructions to determine a least-squares line based on a graphical representation of the rate of change values and the difference values for each of the plurality of data range windows, determine a slope and an intercept of the least-squares line for each of the plurality of data range windows, and determine a corrected slope for each of the slopes of the least-squares lines of each of the plurality of data range windows and determine a best fit function based on a graphical representation of the corrected slopes of the least-squares lines of each of the plurality of data range windows and the reference analyte values at centers of the plurality of data range windows, wherein the best fit function corresponds to a lag characteristic of the analyte sensor.

23. The apparatus of claim 22, wherein the corrected slope is determined based on weighted slopes of the least-squares lines of each of the plurality of data range windows.

24. The apparatus of claim 22, wherein the analyte sensor values are obtained using an analyte sensor that comprises a plurality of electrodes including a working electrode, wherein the working electrode comprises an analyte-responsive enzyme and a mediator, wherein at least one of the analyte-responsive enzyme and the mediator is chemically bonded to a polymer disposed on the working electrode, and wherein at least one of the analyte-responsive enzyme and the mediator is crosslinked with the polymer.

* * * * *

UNITED STATES PATENT AND TRADEMARK OFFICE
CERTIFICATE OF CORRECTION

PATENT NO.        : 8,635,046 B2                                Page 1 of 1
APPLICATION NO.   : 13/166797
DATED             : January 21, 2014
INVENTOR(S)       : Erwin Satrya Budiman It is certified that error appears in the above-identified patent and that said Letters Patent is hereby corrected as shown below:

In the Claims

Column 13, Claim 11, line 38, replace "the continuous analyte" with --the analyte--

Signed and Sealed this
Twenty-ninth Day of April, 2014

Michelle K. Lee
*Deputy Director of the United States Patent and Trademark Office*